United States Patent
Buerger

(10) Patent No.: US 9,936,976 B2
(45) Date of Patent: Apr. 10, 2018

(54) BRACKET FOR EXTERNAL FIXATION OF BONES

(71) Applicant: PBD, Patent & Business Development AG, Zug (CH)

(72) Inventor: Heinz Buerger, Klagenfurt (AT)

(73) Assignee: PBD, Patent & Business Development AG, Zug (CH)

( * ) Notice: Subject to any disclaimer, the term of this patent is extended or adjusted under 35 U.S.C. 154(b) by 0 days.

(21) Appl. No.: 15/402,396

(22) Filed: Jan. 10, 2017

(65) Prior Publication Data
US 2017/0252068 A1 Sep. 7, 2017

Related U.S. Application Data

(60) Provisional application No. 62/301,741, filed on Mar. 1, 2016.

(51) Int. Cl.
*A61B 17/00* (2006.01)
*A61B 17/64* (2006.01)
*A61B 17/56* (2006.01)

(52) U.S. Cl.
CPC ...... *A61B 17/6441* (2013.01); *A61B 17/6425* (2013.01); *A61B 17/6433* (2013.01); *A61B 17/6466* (2013.01); *A61B 2017/00477* (2013.01); *A61B 2017/564* (2013.01)

(58) Field of Classification Search
CPC .. A61B 17/6441; A61B 17/66; A61B 17/6416
See application file for complete search history.

(56) References Cited

U.S. PATENT DOCUMENTS

| 4,488,542 A | * | 12/1984 | Helland | A61B 17/6458 606/54 |
| 4,548,199 A | * | 10/1985 | Agee | A61B 17/1782 606/55 |
| 4,573,459 A | * | 3/1986 | Litton | A61B 17/66 606/58 |
| 4,724,827 A | * | 2/1988 | Schenck | A61H 1/0288 601/40 |

(Continued)

FOREIGN PATENT DOCUMENTS

WO 2007/095429 A1 8/2007
WO 2008/036016 A1 3/2008

OTHER PUBLICATIONS

International Search Report and the Written Opinion of the International Searching Authority dated Apr. 25, 2017 in PCT/EP2017/054753.

*Primary Examiner* — Ellen C Hammond
*Assistant Examiner* — Stuart S Bray
(74) *Attorney, Agent, or Firm* — Collard & Roe, P.C.

(57) ABSTRACT

A fixation system for fixing a bone fracture has a plurality of blocks, needles and rods that snap together in a framework around the fracture. The needles are inserted through the bone on opposite sides of the fracture and the blocks are snapped onto the ends of the needles. Rods are snapped onto the blocks on both sides of the finger to keep the finger in place. Each block has two channels located on opposite sides and extending perpendicular to each other. The channels are structured so that a rod or needle having a diameter equal or slightly greater than one of the channels can be snapped into and retained by the channel.

6 Claims, 2 Drawing Sheets

(56) References Cited

U.S. PATENT DOCUMENTS

| | | | |
|---|---|---|---|
| 4,745,913 A * | 5/1988 | Castaman | A61B 17/60 606/59 |
| 4,895,141 A * | 1/1990 | Koeneman | A61B 17/6416 606/54 |
| 4,978,348 A * | 12/1990 | Ilizarov | A61B 17/6425 606/105 |
| 5,074,865 A * | 12/1991 | Fahmy | A61B 17/6425 606/105 |
| 5,376,091 A * | 12/1994 | Hotchkiss | A61B 17/62 602/22 |
| 5,437,668 A * | 8/1995 | Aronson | A61B 17/62 606/54 |
| 5,653,707 A * | 8/1997 | Taylor | A61B 17/6416 606/54 |
| 5,690,633 A * | 11/1997 | Taylor | A61B 17/8605 606/54 |
| 5,707,370 A * | 1/1998 | Berki | A61B 17/6416 606/55 |
| 5,743,898 A * | 4/1998 | Bailey | A61B 17/171 606/54 |
| 5,746,741 A * | 5/1998 | Kraus | A61B 17/171 606/267 |
| 5,788,695 A * | 8/1998 | Richardson | A61B 17/6458 606/54 |
| 5,810,814 A * | 9/1998 | Newson | A61B 17/6416 606/54 |
| 5,976,125 A * | 11/1999 | Graham | A61B 17/6425 606/32 |
| 5,976,136 A * | 11/1999 | Bailey | A61B 17/6458 606/301 |
| 6,010,501 A * | 1/2000 | Raskin | A61B 17/6416 606/54 |
| 6,024,745 A * | 2/2000 | Faccioli | A61B 17/66 606/54 |
| 6,162,223 A * | 12/2000 | Orsak | A61B 17/6425 606/59 |
| 6,277,118 B1 * | 8/2001 | Grant | A61B 17/6416 606/54 |
| 6,491,694 B1 * | 12/2002 | Orsak | A61B 17/6425 606/57 |
| 9,273,715 B2 * | 3/2016 | Bordeaux | F16B 39/24 |
| 9,539,029 B1 * | 1/2017 | Muniz | A61B 17/6416 |
| 9,622,780 B2 * | 4/2017 | Gerold | A61B 17/6416 |
| 9,622,781 B2 * | 4/2017 | Chang | A61B 17/645 |
| 2002/0013584 A1 * | 1/2002 | Termaten | A61B 17/6425 606/54 |
| 2003/0187432 A1 * | 10/2003 | Johnson | A61B 17/6416 606/59 |
| 2003/0216734 A1 * | 11/2003 | Mingozzi | A61B 17/6416 606/59 |
| 2003/0216739 A1 * | 11/2003 | Ip | A61B 17/68 606/330 |
| 2005/0085754 A1 * | 4/2005 | Werding | A61B 17/6416 602/21 |
| 2005/0261680 A1 * | 11/2005 | Draper | A61B 17/6425 606/59 |
| 2006/0155276 A1 * | 7/2006 | Walulik | A61B 17/6416 606/59 |
| 2006/0229605 A1 * | 10/2006 | Olsen | A61B 17/6416 606/54 |
| 2006/0235383 A1 * | 10/2006 | Hollawell | A61B 17/6416 606/54 |
| 2006/0247621 A1 * | 11/2006 | Waisman | A61B 17/645 606/60 |
| 2007/0038217 A1 * | 2/2007 | Brown | A61B 17/6466 606/57 |
| 2007/0043354 A1 * | 2/2007 | Koo | A61B 17/6416 606/58 |
| 2007/0281283 A1 * | 12/2007 | Lundgren | A61B 17/7008 433/214 |
| 2008/0195095 A1 * | 8/2008 | Renard | A61B 17/6491 606/54 |
| 2009/0024128 A1 * | 1/2009 | Nakamura | A61B 17/6416 606/54 |
| 2009/0054897 A1 * | 2/2009 | Gordon | A61B 17/663 606/57 |
| 2009/0118733 A1 * | 5/2009 | Orsak | A61B 17/60 606/60 |
| 2009/0187189 A1 * | 7/2009 | Mirza | A61B 17/6416 606/59 |
| 2009/0287212 A1 * | 11/2009 | Hirata | A61B 17/6416 606/59 |
| 2011/0034924 A1 * | 2/2011 | Tan | A61B 17/6425 606/59 |
| 2012/0150180 A1 * | 6/2012 | Verma | A61B 17/6416 606/59 |
| 2012/0150181 A1 * | 6/2012 | Dorawa | A61B 17/6466 606/59 |
| 2012/0150182 A1 * | 6/2012 | Dominik | A61B 17/6466 606/59 |
| 2012/0150183 A1 * | 6/2012 | Dorawa | A61B 17/6466 606/59 |
| 2012/0253410 A1 * | 10/2012 | Taylor | A61B 17/6458 606/329 |
| 2013/0110110 A1 * | 5/2013 | Waisman | A61B 17/6458 606/59 |
| 2014/0025075 A1 * | 1/2014 | Hokanson | A61B 17/66 606/58 |
| 2014/0031822 A1 * | 1/2014 | Venturini | A61B 17/64 606/59 |
| 2014/0275959 A1 * | 9/2014 | Disegi | A61B 17/6466 600/410 |
| 2014/0276815 A1 * | 9/2014 | Riccione | A61B 17/6416 606/54 |
| 2015/0127001 A1 * | 5/2015 | Aoki | A61B 17/6425 606/59 |
| 2015/0308478 A1 * | 10/2015 | Oesch | A61B 17/645 403/230 |
| 2015/0342643 A1 * | 12/2015 | Fitzpatrick | A61F 2/28 606/59 |
| 2016/0015426 A1 * | 1/2016 | Dayton | A61B 17/6416 606/57 |
| 2016/0022314 A1 * | 1/2016 | Bordeaux | A61B 17/62 606/56 |
| 2016/0038185 A1 * | 2/2016 | Disegi | A61B 17/6416 606/59 |
| 2016/0095626 A1 * | 4/2016 | Sanders | A61B 17/60 606/59 |
| 2016/0249952 A1 * | 9/2016 | Gerold | A61B 17/6416 606/57 |
| 2016/0270822 A1 * | 9/2016 | Cresina | A61B 17/62 |
| 2016/0310167 A1 * | 10/2016 | Tepic | A61B 17/60 |
| 2016/0367291 A1 * | 12/2016 | Erickson | A61B 17/645 |
| 2017/0071633 A1 * | 3/2017 | Sanders | A61B 17/6416 |
| 2017/0281234 A1 * | 10/2017 | Muniz | A61B 17/64 |

\* cited by examiner

BRACKET FOR EXTERNAL FIXATION OF BONES

CROSS-REFERENCE TO RELATED APPLICATIONS

This application claims priority under 35 USC 119(e) of U.S. Provisional Application Ser. No. 62/301,741, filed on Mar. 1, 2016, the disclosure of which is herein incorporated by reference.

BACKGROUND OF THE INVENTION

1. Field of the Invention

This invention relates to a bracket for external fixation of broken bones. In particular, this invention relates to a snap-on bracket that can hold the horizontal and vertical rods of the fixation brace in place.

2. The Prior Art

When a bone is fractured and requires fixation, the fixation can take place by attaching rods to the bone fragments to put them in place for healing over time. This fixation can take place internally, such as by a rod running through the bone, or externally, via rods placed alongside the exterior of the limb or digit to be fixed. For complex bone fractures it is often necessary to fix the fractured pieces externally. There are a variety of systems available on the market that allow adjusting of angles and distances, mostly by using screws and bolts. For most fractures, these external fixations are suitable. But there is a problem with fractures of small bones, especially fractured fingers. External fixations for finger fractures are miniaturized systems, also using screws. However, there is in most cases not enough room to use these still too bulky fixations. Many surgeons have resorted to using their own concepts. For example, glues such as bone cement are put in place to create the links between the needles that are shot into the bone and the perpendicular fixation rods. But the glues are difficult to handle and require a lot of preparation time as they are usually 2-component systems. And after the glue has been applied, it takes a few minutes to harden. During this time, the surgeon needs to assure that everything stays in the correct position, which is difficult and time-consuming.

SUMMARY OF THE INVENTION

It is therefore an object of the invention to provide a bracket for attaching the pins or screws extending from the bone fragments to an external rod. It is another object of the invention to provide a fixation system that is simple and inexpensive to use, and is effective for fixing fractures in small bones.

These and other objects are accomplished by a fixation system for fixing a fracture in one or more bones, comprising a plurality of blocks, needles and rods that snap together in a framework around the fracture. The needles are inserted through the bone on opposite sides of the fracture, such that the needles extend entirely through the finger on both sides. The blocks are snapped onto the needles, and then rods are snapped onto the blocks on both sides of the finger to create a rigid framework to keep the finger in place.

Each block has a first channel extending in a first direction and being open to a first surface of the block, and a second channel extending in a second direction and being open to a second surface of the block. The first surface and second surface are located opposite each other and the first channel is arranged perpendicular to the second channel. This way the needles and rods can be snapped onto the block on opposite sides of the block so that they extend perpendicular to each other. The channels are structured so that a width of the channel at each of the first and second surfaces is less than a diameter of the channel, so that a rod or needle having a diameter equal or slightly greater than one of the channels can be snapped into and retained within the respective channel.

The first and second channels have different diameters— one channel being dimensioned to hold the needles running through the bones, and the other channel being dimensioned to hold the exterior rods.

The bracket is preferably made of molded polyurethane. The bracket can be manufactured by creating a prototype via 3-D printing, then molding silicon around the prototype in a mold to create a mold cavity in the shape of the desired block.

Generally, the needles are manufactured from surgical steel, titanium or other suitable metal, and the rods can be made of reinforced carbon fiber, which is invisible to X-rays, so that visualization of the fracture is easier.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
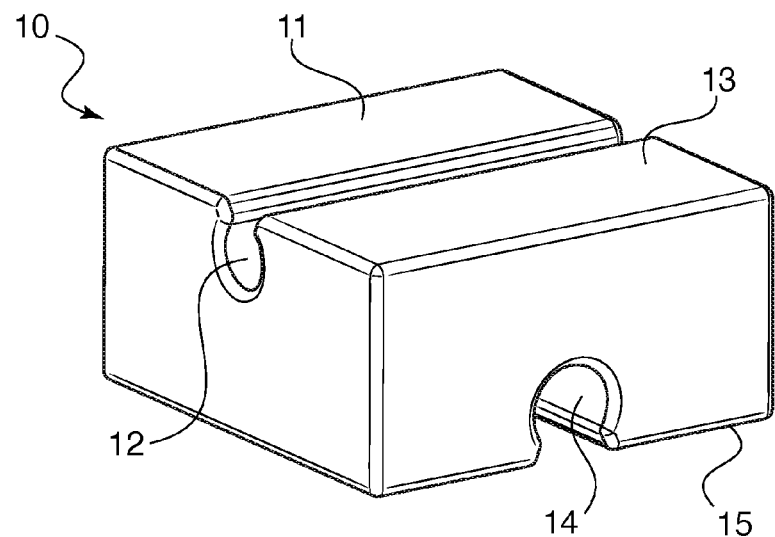
FIG. 1 shows the bracket according to the invention.

Referring now in detail to the drawings, FIG. 1 shows the bracket 10 for use in the system according to the invention. Bracket 10 consists of a block 11 having a first channel 12 located on a first surface 13, and a second channel 14 located on a second surface 15. Surface 13 and surface 15 are located on opposite sides of block 11. Channel 12 and channel 14 extend perpendicular to each other. The shape of channels 12 and 13 is roughly circular, with the opening onto surfaces 13 and 15 being smaller than a diameter of the respective channel. This shape ensures that a needle or rod inserted into the channel is retained in the channel. Block 11 is preferably formed from polyurethane, but other materials could be used. Block 11 is preferably molded and can be manufactured by 3D printing a model, pouring silicone around the model in a mold to create the mold cavity, and then molding the block using polyurethane in the silicone mold. Any other suitable manufacturing methods could be used as well.

Figure 2:
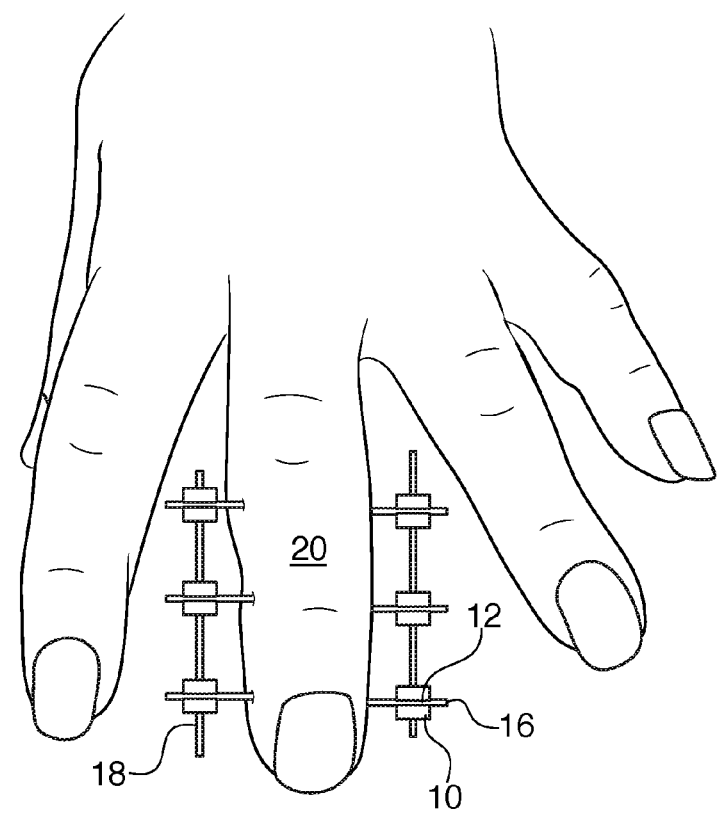
FIG. 2 shows a finger being fixed using the fixation system according to the invention.
Figure 3:
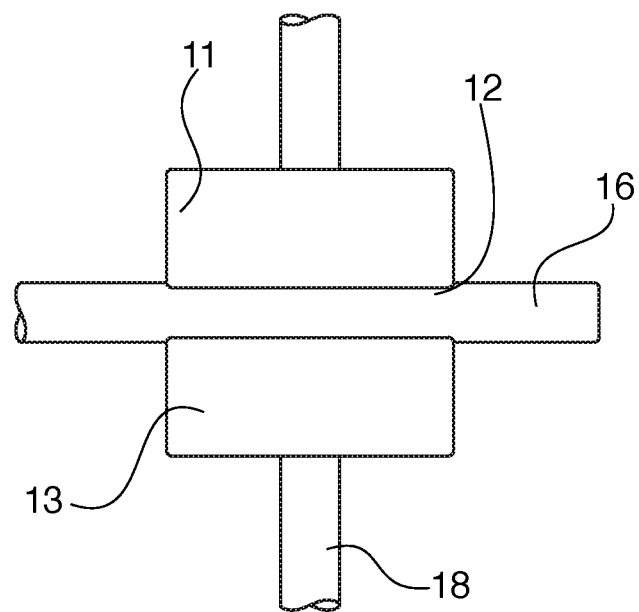
FIG. 3 shows a top view of a bracket according to the invention holding a pin and a rod from the fixation system.
Figure 4:
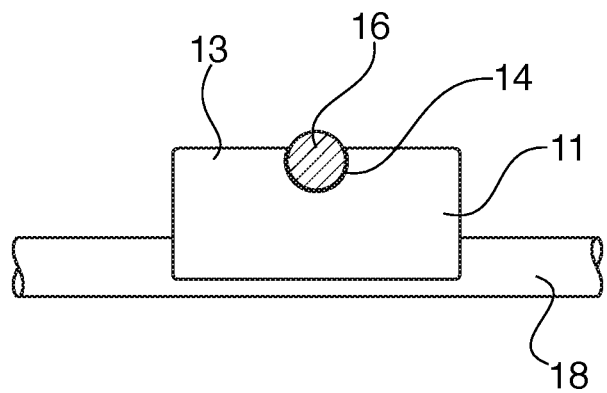
FIG. 4 is a side view of the arrangement of FIG. 3.

FIG. 2 shows a view of the fixation system according to the invention in used on a finger 20. Here, needles 16 are inserted through the bones in the finger and are then attached to brackets 10 by snapping them into channels 14. Glue can also be added for extra stabilization, but is not necessary. Rods 18 are also attached to blocks 10 by snapping them into channels 14. FIGS. 3 and 4 show enlarged views of the rods 18 and needles 16 attached to brackets 10. Preferably, rods 18 and needles 16 have diameters that are just slightly larger than the diameters of channels 14 and 12, respectively, so that the rods and needles are held in the channels with friction fit. The needles are usually a standard size in all hospitals (0.8 mm or 1.0 mm). The rod preferably has a diameter of 1.2 mm. The brackets can be molded with channels of any specified size.

The present invention provides a simple and inexpensive way to connect the needles and fixation rods to stabilize a fracture in a finger. The brackets can be quickly and easily attached to the needles and rods with little movement. This system is ideal for fixing small bones, as the brackets occupy very little space, and are lightweight.

Accordingly, while only a few embodiments of the present invention have been shown and described, it is obvious that many changes and modifications may be made thereunto without departing from the spirit and scope of the invention.

What is claimed is:

1. A fixation system for fixating a fracture in one or more bones of a finger, comprising:
    a plurality of needles adapted to be placed through the bones and extending out of the finger on two opposite sides of the bones;
    two rods configured to extend on opposite sides of the finger; and
    a plurality of brackets each bracket comprising a block having a first channel extending in a first direction and being open to a first surface of the block, and having a second channel extending in a second direction and being open to a second surface of the block, wherein the first surface and second surface are located opposite each other, wherein the first channel is arranged perpendicular to the second channel, and wherein a width of the channel at each of the first and second surfaces is less than a diameter of the corresponding channel, wherein the first channel of each bracket is dimensioned to hold the needles and the second channel of each bracket is dimensioned to hold the rods, such that each of the needles is connected to the rods on both ends of the needles via the brackets by snapping the needles into the respective first channels and snapping the rods into the respective second channels of the brackets.

2. The fixation system according to claim 1, wherein there are three needles and six brackets.

3. The fixation system according to claim 1, wherein the rods are made of reinforced carbon fiber.

4. A method of fixing a broken bone in a finger comprising:
    placing a plurality of needles through the bone on opposite sides of the fracture such that the needles extend through the finger on both sides of the bone;
    connecting each of the ends of each of the needles to a bracket comprising a block having a first channel extending in a first direction and being open to a first surface of the block, and having a second channel extending in a second direction and being open to a second surface of the block,
        wherein the first surface and second surface are located opposite each other,
        wherein the first channel is arranged perpendicular to the second channel, and wherein a width of the channel at each of the first and second surfaces is less than a diameter of the corresponding channel,
        wherein the step of connecting comprises snapping each end of each needle into the first channel of each block;
    connecting each block on one side of the finger to a first rod by snapping the rod into the second channel of each block on said one side; and
    connecting each block on the opposite side of the finger to a second rod by snapping the second rod into the second channel of each block on said opposite side.

5. The method according to claim 4, wherein the first and second rods are made of reinforced carbon fiber.

6. The method according to claim 4, further comprising applying glue to the rods and needles or channels in the block.

* * * * *